US011513089B2

(12) United States Patent
Van Ingelgem et al.

(10) Patent No.: US 11,513,089 B2
(45) Date of Patent: Nov. 29, 2022

(54) SYSTEMS AND METHODS FOR CONDUCTING ELECTROCHEMICAL IMPEDANCE SPECTROSCOPY

(71) Applicants: VRIJE UNIVERSITEIT BRUSSEL, Brussels (BE); KATHOLIEKE UNIVERSITEIT LEUVEN, Leuven (BE)

(72) Inventors: Yves Van Ingelgem, Landen (BE); Bart Landuyt, Vissenaken (BE); Sven Verguts, Sint-Joost-ten-Node (BE)

(73) Assignees: VRIJE UNIVERSITEIT BRUSSEL, Brussels (BE); KATHOLIEKE UNIVERSITEIT LEUVEN, Leuven (BE)

( * ) Notice: Subject to any disclaimer, the term of this patent is extended or adjusted under 35 U.S.C. 154(b) by 1203 days.

(21) Appl. No.: 16/063,070

(22) PCT Filed: Dec. 18, 2016

(86) PCT No.: PCT/EP2016/081627
§ 371 (c)(1),
(2) Date: Jun. 15, 2018

(87) PCT Pub. No.: WO2017/103244
PCT Pub. Date: Jun. 22, 2017

(65) Prior Publication Data
US 2019/0204250 A1 Jul. 4, 2019

(30) Foreign Application Priority Data

Dec. 17, 2015 (GB) .................................... 1522323

(51) Int. Cl.
*G08B 21/04* (2006.01)
*G01N 27/02* (2006.01)
(Continued)

(52) U.S. Cl.
CPC ............ *G01N 27/026* (2013.01); *B01L 1/025* (2013.01); *B01L 3/5085* (2013.01);
(Continued)

(58) Field of Classification Search
USPC ... 340/539.12, 539.11, 539.13, 539.3, 545.6, 340/574, 575, 602, 636.17, 656, 680–682
See application file for complete search history.

(56) References Cited

U.S. PATENT DOCUMENTS 8,211,313 B2 * 7/2012 Fritchie ................ G01N 33/721
436/526
2002/0164778 A1 * 11/2002 Kajiyama ............ C12Q 1/6837
435/287.2
(Continued)

FOREIGN PATENT DOCUMENTS

CN        1902305 A     1/2007
CN    102973267 A     3/2013
(Continued)

OTHER PUBLICATIONS

Written Opinion from SG Application No. 11201804971V, dated Aug. 2, 2019.
(Continued)

*Primary Examiner* — Daniel Previl
(74) *Attorney, Agent, or Firm* — Workman Nydegger

(57) ABSTRACT

A system for measuring electrical characteristics of bioparticles is described. The system comprises an incubator for performing electrochemical measurements in a defined environment and a substrate holder positioned in said incubator for holding a substrate comprising a plurality of wells. The system is furthermore configured for continuously or regularly measuring electrochemical data. The system also comprises a processing means for comparing the continuously or regularly measured electrochemical data with reference data (Continued)

and for determining a moment for adding an active compound based on said comparison.

17 Claims, 8 Drawing Sheets

(51) Int. Cl.
 *B01L 3/00* (2006.01)
 *G01N 33/483* (2006.01)
 *B01L 1/02* (2006.01)

(52) U.S. Cl.
 CPC .... *G01N 33/4836* (2013.01); *B01L 2200/143* (2013.01); *B01L 2300/0645* (2013.01); *B01L 2300/0829* (2013.01); *B01L 2300/0851* (2013.01)

(56) References Cited

U.S. PATENT DOCUMENTS

| | | | | |
|---|---|---|---|---|
| 2003/0004394 | A1* | 1/2003 | Carpay | B01L 3/5025 600/22 |
| 2004/0096926 | A1* | 5/2004 | Packard | G01N 33/542 435/23 |
| 2004/0171034 | A1* | 9/2004 | Agnew | G01N 33/502 435/7.1 |
| 2004/0215052 | A1* | 10/2004 | Kullik | G05D 11/138 600/22 |
| 2005/0112544 | A1 | 5/2005 | Xu et al. | |
| 2006/0050596 | A1 | 3/2006 | Abassi et al. | |
| 2006/0105449 | A1 | 5/2006 | Larmer et al. | |
| 2006/0216203 | A1 | 9/2006 | Fuller et al. | |
| 2010/0028925 | A1* | 2/2010 | Rocco | C12Q 1/42 435/21 |
| 2012/0153221 | A1 | 6/2012 | Wauters et al. | |
| 2014/0273191 | A1* | 9/2014 | Tipgunlakant | C12M 23/12 435/303.1 |
| 2014/0356849 | A1* | 12/2014 | Wikswo | B01L 3/5027 435/284.1 |
| 2015/0004077 | A1* | 1/2015 | Wikswo | C12M 29/10 422/502 |

FOREIGN PATENT DOCUMENTS

| | | |
|---|---|---|
| GB | 2386949 A | 10/2003 |
| GB | 2435769 A | 9/2007 |
| JP | 2008534965 A | 8/2008 |
| JP | 2009244197 A | 10/2009 |
| WO | 03001889 A2 | 1/2003 |
| WO | 2004010103 A2 | 1/2004 |
| WO | 2005059513 A2 | 6/2005 |
| WO | 2006104839 A2 | 10/2006 |
| WO | 2008036375 A2 | 3/2008 |
| WO | 2009137440 A1 | 11/2009 |

OTHER PUBLICATIONS

Great Britain Search Report from GB Application No. GB 1522323.3, dated Jun. 10, 2016.
International Search Report from PCT Application No. PCT/EP2016/081627, dated Mar. 28, 2017.
Office Action from corresponding Chinese Application No. 201680081922, dated Jun. 1, 2020.
Office Action from corresponding Japanese Application No. 2018-530733, dated Sep. 24, 2020.
Rahman et al., "Cell Culture Monitoring by Impedance Mapping using a Multielectrode Scanning Impedance Spectroscopy System (CellMap)," Physiological Measurement, vol. 29, Jun. 10, 2008, pp. S227-S239.
Das et al., "Evaluation of Single Cell Electrical Parameters from Bioimpedance of a Cell Suspension," Royal Society of Chemistry, Feb. 26, 2014, vol. 4, pp. 18178-18185.
Search Report from corresponding European Application No. 16822442.6, dated Oct. 27, 2021.

* cited by examiner

SYSTEMS AND METHODS FOR CONDUCTING ELECTROCHEMICAL IMPEDANCE SPECTROSCOPY

FIELD OF THE INVENTION

The invention relates to the field of biosensing of living cells. More specifically it relates to methods and systems for conducting electrochemical impedance spectroscopy (EIS) on living cells in wells.

BACKGROUND OF THE INVENTION

Electrochemical impedance spectroscopy (EIS) methods are used to investigate cell cultures in a non-invasive manner. For this purpose often cell cultures are grown in wells that have 2 electrodes on the bottom surface. The approach in general consists of adding an active compound to the cell culture in these wells after an initial stage of cell growth. From that moment on the evolution of the response is followed in order to learn something about the effect of the active compound on the cells in the well. This in turn will provide information on the working mechanism of the active compound.

Cell culture growing in a well will present a specific growth path, maximizing at the moment where the entire bottom is densely packed with a layer of cells. This growth path depends on the geometry of the well, but also on the entire procedure of preparing, counting and administering the cells to the measuring as well as on external conditions such as temperature, atmosphere composition, etc. As such the growth process kinetics can differ for each experiment.

In order to obtain reliable results, the quality and reproducibility of the measurements is essential.

One of the factors influencing the reliability of electrochemical impedance spectroscopy for measurements on cell cultures is the exact moment in time the (potentially) active compound is added to the cell culture. If the active compound is added too early, the growth kinetics and the interaction with the active compound will interfere too much, resulting in a disturbed measurement. On the other hand adding the active compound too late will result in cells that are already dying due to cell growth competition.

Electrochemical measurements typically are performed in multiple well plates. The measurements in the different wells are based on electrodes in the wells that are lead to the edge or edges of the well plate and further lead to a driving and/or read-out circuitry. Although the electrodes in the wells typically are identical over the wells, the leads connecting the electrodes in the well with the electrical contact points at the edge of the well plate show large differences in geometry, size and/or length, amongst others due to the different positions of the wells on the well plate. The test setup relying on multiple wells where the electrodes are connected to the analyzer through differing leads thus intrinsically introduces variability in the readout between different wells on the same plate. This variability depending on the position of the well plate hence induces an additional uncertainty on the readout obtained using the instrument. This has a negative impact on the quality and reliability of the readout of the device and thus on the confidence with which the processes taking place in each individual well can be identified and quantified.

In practice this variability in impedance measurements is presently countered by using a number of the wells in the well plate as reference wells. These will be filled with only medium, not with cells or active compounds. The data collected from these wells are typically used for calibration purposes in the subsequent data analysis and will not directly contribute to an improved understanding of the behavior of the cells or compounds present in the setup.

The impedance of the cell culture is determined by alternatingly measuring the impedance in one of the wells at a frequency range between 1 and 100 kHz. A lot of valuable information is however contained in a lower frequency range. Measuring in a lower frequency range however means that the measurement time for each individual well is increased. As such the resolution in time with which the culture in an individual well is followed is drastically reduced if measurements are also performed in the lower frequency range. The time resolution is however essential in capturing relevant effects taking place in living cell cultures related to their interaction with added compounds, thus introducing a difficult trade off between obtaining qualitative data and optimizing time resolution. An unambiguous interpretation of the results requires high-quality measurements. The quality of the measurements is partially determined by the experimental hardware, but also by external influences. During the data collection for example the measuring well plate is located inside an incubator with regulated conditions such as temperature, atmosphere. In practice however the conditions inside the incubator may vary in the course of an experiment (temperature fluctuations, shocks . . . ). These influences do have an effect on the cell behavior and thus are translated into the data obtained. From that moment on the response of the cell to the added compound is convoluted with the cell's response to the fluctuations or changes in external conditions. This can significantly influence the data interpretation and quality of the results in a negative way and thus has to be avoided.

There is a need for systems and methods for conducting electrochemical characterization which solve one or more of the above problems.

SUMMARY OF THE INVENTION

It is an object of the present invention to provide methods and systems for conducting electrochemical characterization of bioparticles, such as for example cells, organelles, exosomes or viruses, based on a robust but sensitive data acquisition.

The above objective is accomplished by a method and device according to the present invention.

The present invention relates to a system for measuring electrical characteristics of bioparticles, the system comprising an incubator for performing electrochemical measurements in a defined environment, a substrate holder positioned in said incubator for holding a substrate comprising a plurality of wells, wherein the system is configured for continuously or regularly measuring electrochemical data, the system comprising a processing means for comparing the continuously or regularly measured electrochemical data with reference data and for determining a moment for adding an active compound based on said comparison.

The system furthermore may comprise a delivery means for automatically delivering an active compound in the well at the determined addition moment.

The system may be adapted for measuring impedance data over a frequency span of at least two decades, at least 2 measurement points per decade being recorded. The frequency span may be at least 5 decades. The number of measurement points recorded per decade may be at least 3 or may be at least 4).

The processing means may be adapted for determining the moment for adding an active compound based on a parameter value derived from a broad-spectrum impedance measurement conducted on the bioparticles in the well.

The broad-spectrum impedance measurement may correspond with an impedance measurement spanning at least a frequency range of 100 Hz to 50 kHz, e.g. at least a frequency range of 10 Hz to 80 kHz, for example at least a frequency range of 1 Hz to 100 kHz.

The system may be adapted for measuring impedance data comprising both a magnitude |Z| as well as a phase Q of the impedance, with phase angle θ.

The system may be adapted for measuring electrochemical data on bioparticles in solution. It is an advantage of embodiments of the present invention that bioparticles in solution can be characterized.

The processing means may be adapted for deriving information regarding a specific phenomenon.

The processing means may be a switchable module adapted for deriving information regarding one of the following phenomena: toxicity of a compound for cells, Receptor activation and inhibition such as G Protein Coupled Receptors (GPCRs), Receptor Tyrosine Kinases (RTKs), Ion Channels (ICs), Nuclear Receptors (NRs), the dissection of signal transduction cascades, microbial biofilm formation/inhibition/destruction or viral mode of entry and total viral load. Receptor activation and inhibition may include activation and inhibition of G Protein Coupled Receptors (GPCRs), of Receptor Tyrosine Kinases (RTKs), of Ion Channels (ICs) or of Nuclear Receptors (NR). It is an advantage of at least some embodiments of the present invention that both the quality of the data that is collected and the amount of information that is obtained is improved compared to conventional systems. It is an advantage of at least some embodiments of the present invention that costs as well as measurement duration can be reduced compared to conventional EIS measurements.

It is an advantage of at least some embodiments of the present invention that an automated interpretation of the results can be performed, which does not depend on the skill of the person performing the interpretation. It is an advantage of embodiments of the present invention that the conclusion about the process taking place can have a statistics-based significance level.

It is an advantage of at least some embodiments of the present invention that environmental parameters such as for example temperature fluctuations, shocks, atmosphere, etc. can be monitored and can be taken into account for interpretation of the measurement results obtained. Such parameters may be measured on the substrate or in the incubator.

The processing means may be adapted for determining said information regarding said phenomenon, taking into account said determined addition moment for delivering the active compound in the well.

The system furthermore may comprise an environmental parameter sensor for sensing an environmental parameter in the incubator, the environmental parameter being one or more of a temperature, a humidity, a $CO_2$ level, an $O_2$ level, a pH, a salinity, a nutrient concentration, and a degree of illumination.

The processing means may be adapted for determining said information regarding said phenomenon, taking into account said environmental parameter.

The system furthermore may comprise a plurality of driving and/or read-out circuitries for separately driving and/or reading out different wells or groups of wells through different circuitries, an electrical connecting means for connecting said plurality of driving and/or read-out circuitry with different electrodes of individual wells or different groups of wells of the substrate by connecting to their different electrical connection points at a backside of the substrate.

The driving and/or read-out circuitries may be positioned substantially under the different wells or under the different groups of wells under the substrate, when the substrate is positioned in the substrate holder, such that the electrical circuits can be short and substantially the same for the different wells or different groups of wells.

The driving and/or read-out circuits may be configured for reading out different well or different groups of wells in parallel in time, i.e. simultaneously.

Each driving and/or read-out circuit may comprise an analog to digital converter and a data acquisition component.

The system may be adapted for acquiring electrochemical measurement data of a well and processing the data not taking into account calibration data of another well in the substrate.

The present invention also relates to a method for measuring electrical characteristics of bioparticles, the method comprising continuously or regularly measuring electrochemical data on the bioparticles in a defined environment, comparing the continuously or regularly measured electrochemical data with reference data, determining a moment for adding an active compound based on said comparison, and adding the active compound on the determined moment.

Continuously or regularly measuring electrochemical data may comprise measuring impedance data over a frequency span of at least two decades, at least 2 measurement points per decade being recorded. The frequency span may be at least 5 decades. The number of measurement points recorded per decade may be at least 3 or may be at least 4.

Determining the moment for adding an active compound may be based on a parameter value derived from a broad-spectrum impedance measurement conducted on the bioparticles in the well.

The broad-spectrum impedance measurement may correspond with an impedance measurement spanning at least a frequency range of 100 Hz to 50 kHz, e.g. at least a frequency range of 10 Hz to 80 kHz, for example at least a frequency range of 1 Hz to 100 kHz.

Measuring electrochemical data may comprise measuring impedance data comprising both a magnitude as well as a phase of the impedance.

The method may comprise deriving information regarding a specific phenomenon.

The method may comprise deriving information regarding one of the following phenomena: toxicity of a compound for cells, Receptor activation and inhibition such as G Protein Coupled Receptors (GPCRs), Receptor Tyrosine Kinases (RTKs), Ion Channels (ICs), Nuclear Receptors (NRs), the dissection of signal transduction cascades, microbial biofilm formation/inhibition/destruction or viral mode of entry and total viral load.

The method may comprise determining said information regarding said phenomenon, taking into account said determined addition moment for delivering the active compound in the well.

The method may comprise sensing an environmental parameter in the incubator, the environmental parameter being one or more of a temperature, a humidity, a $CO_2$ level, an $O_2$ level, a pH, a salinity, a nutrient concentration, and a degree of illumination.

The method may comprise determining said information regarding said phenomenon, taking into account said environmental parameter.

The method may comprise reading out different well or different groups of wells in parallel in time, i.e. simultaneously.

The method may comprise acquiring electrochemical measurement data of a well and processing the data not taking into account calibration data of another well in the substrate.

The present invention also relate to a computer program product for measuring electrical characteristics of bioparticles, the computer program product being adapted for, when run on a computing means, performing a method as described above.

The present invention also relates to the use of a system as described above for monitoring growth of adherent cell cultures.

The present invention also relates to the use of a system as described above for monitoring growth of suspended cell cultures.

In another aspect, the present invention relates to a substrate for measuring bioparticle electrical characteristics in individual wells, the substrate comprising a plurality of individual wells, for at least two individual wells or at least two groups of wells, at least two electrodes per well for electrically characterizing an electrical parameter of bioparticles in a well, electrical leads for providing a conductive path through the substrate between the electrodes of each well and electrical connection points at a back of the substrate, and electrical connection points for connecting the at least two individual wells or at least two groups of wells separately to a driving and/or read-out circuit.

The bioparticles may for example be cells, organelles, exosomes, viruses, etc.

It is an advantage of embodiments of the present invention that the electrical circuits connecting the electrodes of the individual wells with the driving and/or read-out circuitry can be made less differing from each other, e.g. in length, such that differences in influences of the electrical path can be reduced and more accurate measurements can be obtained.

It is an advantage of embodiments of the present invention that the length of the electrical paths used can be reduced by providing electrical leads that pass through the substrate and by providing electrical connection to a driving and/or read-out circuitry at the backside of the substrate. Since the different leads do not need to run over the length of the substrate, the differences in length for the different leads can be reduced. A reduced length thereby means a reduction in the potential pick up of external noise, resulting in an improvement in data quality and hence measurement result.

For each of the individual wells electrical connection points may be provided substantially below the individual wells for connection to a driving and/or read-out circuitry separately. It is an advantage of embodiments of the present invention that the different wells can be connected in substantially the same way to the driving and/or read-out circuitry, resulting in an improvement in data quality.

It is an advantage of embodiments of the present invention that the different wells can be driven and/or read-out substantially in parallel, resulting in a gain in time resolution for the measurements.

It is an advantage of embodiments of the present invention that less or no wells are required for calibrating the wells for compensating for differences in the circuits for driving and/or read-out circuitry. The latter results in the possibility of using more wells for actual measurements.

Said at least two groups of wells may be groups consisting of neighboring wells wherein the distance between the neighboring wells within one group is not larger than the distance between wells of different groups of wells.

It is an advantage of embodiments of the present invention that the length of the circuits for driving and/or read-out circuitry can be relatively short for all wells.

The substrate may furthermore comprise an environmental parameter sensor for sensing environmental parameters, the environmental parameter being one or more of a temperature, a humidity, a $CO_2$ level, an $O_2$ level, salinity, nutrient concentration, illumination and pH.

It is an advantage of embodiments of the present invention that environmental parameters can be taken into account for controlling the conditions under which the processes are performed.

The present invention also relates to a system for measuring bioparticle electrical characteristics such as for example electrochemical impedance spectra, the system comprising an incubator for performing electrochemical measurements in a defined environment, a substrate holder positioned in said incubator for holding a substrate as described above, a plurality of driving and/or read-out circuitries for separately driving and/or reading out different wells or groups of wells through different circuitries, an electrical connecting means for connecting said plurality of driving and/or read-out circuitry with different electrodes of individual wells or different groups of wells of the substrate by connecting to their different electrical connection points at a backside of the substrate.

Further features and advantages may correspond with optional features and advantages as described for the first aspect.

The present invention also relates to a substrate for measuring electrical characteristics of bioparticles, such as for example cells, organelles, exosomes or viruses, in individual wells, the substrate comprising a plurality of individual wells, for each of said wells at least two electrodes for electrically characterizing an electrical parameter of bioparticles in a well, said substrate furthermore comprising an environmental parameter sensor for sensing an environmental parameters, the environmental parameter being one or more of a temperature, a humidity, a $CO_2$ level, an $O_2$ level, a pH, a salinity, a nutrient concentration, and a degree of illumination.

The present invention also relates to a system for measuring electrical characteristics of bioparticles, such as for example cells, organelles, exosomes or viruses, the system comprising an incubator for performing electrochemical measurements in a defined environment, a substrate holder positioned in said incubator for holding a substrate, wherein the system furthermore comprises a data collection means for collecting an environmental parameter from an environmental parameter sensor positioned on the substrate in the substrate holder or from an environmental parameter sensor provided in the incubator, wherein the environmental parameter is any of a temperature, a humidity, a $CO_2$ level, an $O_2$ level, a pH, a salinity, a nutrient concentration, and a degree of illumination.

Further features and advantages may correspond with optional features and advantages as described for the first aspect.

The present invention also relates to a system for measuring electrical characteristics of bioparticles, such as for example cells, organelles, exosomes or viruses, the system comprising
an incubator for performing electrochemical measurements in a defined environment,
a substrate holder positioned in said incubator for holding a substrate,
wherein the system comprises a processing means adapted for receiving the electrochemical measurement data and for deriving information regarding a specific phenomenon.

Further features and advantages may correspond with optional features and advantages as described for the first aspect.

The present invention also relates to a computer program product for deriving information on a phenomenon, based on measurement of electrical characteristics of bioparticles and based on
an environmental parameter measured at the substrate, or information regarding a determined moment when the active compound was added to the bioparticles.

The phenomenon may be one or more of the following phenomena: toxicity of a compound for cells, receptor activation and inhibition, dissection of signal transduction cascades, microbial biofilm formation/inhibition/destruction, and viral mode of entry and/or total viral load. Receptor activation and inhibition may include activation and inhibition of G Protein Coupled Receptors (GPCRs), of Receptor Tyrosine Kinases (RTKs), of Ion Channels (ICs) or of Nuclear Receptors (NR).

In one aspect, the present invention also relates to a system for measuring electrical characteristics of bioparticles, the system comprising an incubator for performing electrochemical measurements in a defined environment, a substrate holder positioned in said incubator for holding a substrate comprising a plurality of wells, wherein the system is configured measuring impedance data over a frequency span of at least two decades, at least 2 measurement points per decade being recorded. The frequency span may be at least 5 decades. The number of measurement points recorded per decade may be at least 3 or may be at least 4). The broad-spectrum impedance measurement may correspond with an impedance measurement spanning at least a frequency range of 100 Hz to 50 kHz, e.g. at least a frequency range of 10 Hz to 80 kHz, for example at least a frequency range of 1 Hz to 100 kHz.

The system may be adapted for measuring impedance data comprising both a magnitude |Z| as well as a phase Q of the impedance, with phase angle θ.

The system may be adapted for measuring electrochemical data on bioparticles in solution. It is an advantage of embodiments of the present invention that bioparticles in suspension can be characterized.

Further features and advantages may correspond with optional features and advantages as described for the first aspect.

The present invention also relates to a method for measuring electrical characteristics of bioparticles, the method comprising measuring electrochemical data over a frequency span of at least two decades, at least 2 measurement points per decade being recorded. The frequency span may be at least 5 decades. The number of measurement points recorded per decade may be at least 3 or may be at least 4. The measurement may be performed over a broad-spectrum. The broad-spectrum impedance measurement may correspond with an impedance measurement spanning at least a frequency range of 100 Hz to 50 kHz, e.g. at least a frequency range of 10 Hz to 80 kHz, for example at least a frequency range of 1 Hz to 100 kHz.

Measuring electrochemical data may comprise measuring impedance data comprising both a magnitude |Z| as well as a phase Q of the impedance, with phase angle θ.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
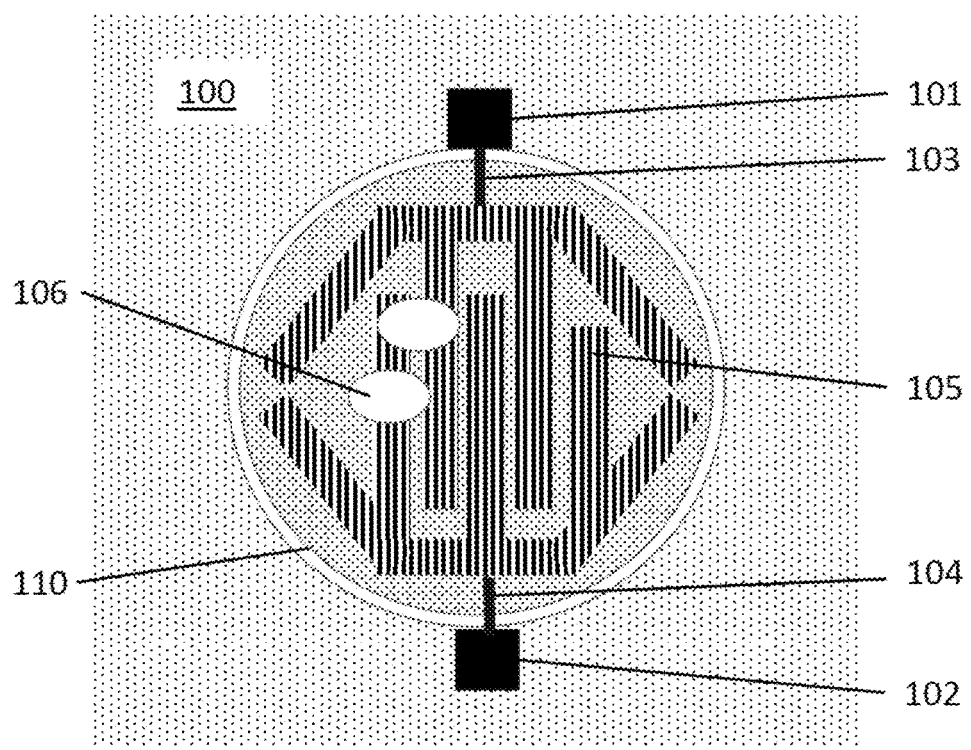
FIG. 1 shows the front, or top, view of a well comprising containing means and an electrode array as sensing element.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "substrate", reference is made to a set of positions comprising sensing elements and contention means. For example, the substrate may comprise a single piece, or a stacked plate comprising connectable pieces. The substrate may be a well plate. The substrate also may be a substrate comprising stacked wells.

Where in embodiments of the present invention reference is made to "sensing elements", reference is made to a cell or part of a sensing circuit which interacts with a sample to obtain a response and measure it. For example, a sensing element which will be discussed with reference to the present invention include, but are not limited to, an "electrode array", which may comprise a set of electrodes, for example at least two electrodes forming an anode and a cathode. Such sensing element is suitable for measuring electric characteristics of a sample, such as capacitance, inductance, and others.

In a first aspect, the present invention relates to a system for performing measurements for example electrochemical measurement, on samples such as biological samples, in a defined environment. The system comprises an incubator for performing electrochemical measurements in a defined environment, a substrate holder positioned in said incubator for holding a substrate comprising a plurality of wells, wherein the system is configured for continuously or regularly measuring electrochemical data. The system comprises a processing means for comparing the continuously or regularly measured electrochemical data with reference data and for determining a moment for adding an active compound based on said comparison.

The system thus is configured for continuously or regularly (e.g. at selected or predetermined time intervals such that a view on the dynamics is obtained) measuring electrochemical data, and reference data may be included in a memory. This can be used, for example, to signalize when an active compound should be added during measurement of a reaction. In one aspect, the present invention also relates to a system for measuring electrical characteristics of bioparticles, wherein the system is configured for continuously measuring electrochemical data, the system further comprising a processing means for comparing the continuously measured electrochemical data with reference data and for determining a moment for adding an active compound based on said comparison. The latter is advantageous since, in order to obtain measurements of a quality that is as high as possible, it is important to add the active compounds at exactly the right moment to increase the reliability. The higher the reliability, the more the drug development process can be optimized. The exact moment (in hours and minutes after adding the cell cultures to the measuring well) may differ for bioparticle type, lab conditions, incubator parameters . . . To reduce the potential scatter on the recorded data, embodiments of the present invention thus may make use of an on-line measuring method for determining the moment of addition. In some examples of embodiments of the present invention, a parameter value derived from a broad-spectrum impedance measurement conducted on the bioparticles in the well from the initiation of the experiment may be used for determining the moment of addition. The value of this parameter is determined through continuous, repeated measurements. Its evolution in time may be followed up and when the curve describing its evolution resembles a specific, pre-determined curve, the ideal moment for adding the active compound to the culture was reached. In other words, the moment in time for adding the active compound may be determined by comparing the continuously or repetitive measured electrical characteristic with reference data. This process may be automatized. For example, the system may comprise means for automatically deciding when to add. The system also may comprise means for automatically adding active compound via delivery means, such as for example a multi-channel pipette. Thus, at the determined moment the active compound may be automatically added by a device that is connected through a feedback loop with the acquisition equipment. Alternatively a signal may be provided to a human operator that adds the correct amount of compound to the measuring wells. According to embodiments of the present invention, in the subsequent analysis of the bioparticles behavior may make use this point in time (adding of active compound) as the reference point for the investigation of the effects of the compound on the cell culture. In such embodiments, use can even be made of conventional well plates with conventional electrical paths for the different wells, but the characterizing features is the fact that the process is continuously monitored and use is made thereof to define when the active compound is to be delivered to the bioparticles. In the process of decision, optionally also data of sensors sensing environmental parameters may be taken into account.

Figure 8:
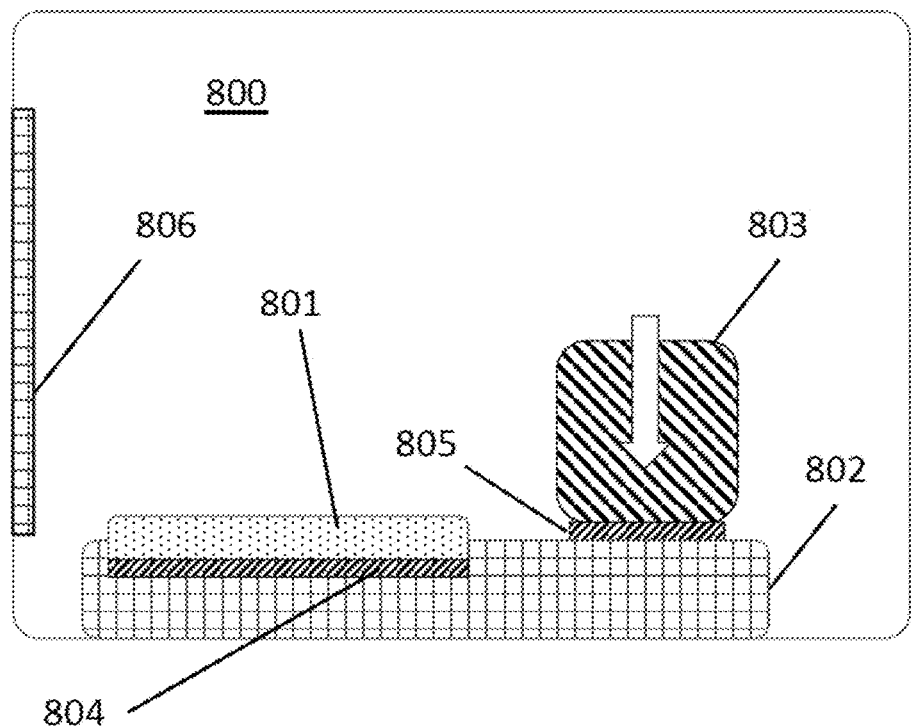
FIG. 8 shows an exemplary embodiment of an incubator including a holder for a modular substrate and a modular CPU.

By way of illustration, embodiments of the present invention not being limited thereto, standard and optional features of the system are further discussed below. FIG. 8 shows an exemplary of the system, which may comprise an incubator 800, within which a substrate, e.g. a well plate, 801 may be placed. This incubator 800 may ensure that any sample, such as cells, organelles, exosomes or viruses contained in the contention zone (e.g. in the wells) are kept under controlled conditions, such as temperature, humidity and level of $CO_2$ and/or $O_2$, a pH, a salinity, a nutrient concentration, and a degree of illumination. These elements may influence the cell growth and can also have an influence on the interaction between the cells and any compound, such as an active compound, added to the cells in the wells. As will be further elaborated, the incubator may include means for measuring environmental parameters and means for changing and controlling these. Whereas it has been described above that an environmental sensor may be part of the substrate, alternatively or in addition thereto, such an environmental sensor also may be introduced directly in the system 800 or alternatively may not be present.

The system according to embodiments of the present invention comprises a substrate holder 802 for holding the substrate. A connector 804 with, for example, dedicated connections typically may be provided between the substrate 801 and the substrate holder 802 or may be part of the substrate holder. The connector thus may be dedicated for connecting to the substrate and for providing/capturing drive/read-out signals to a substrate 801 as described in the first aspect.

Figure 9:
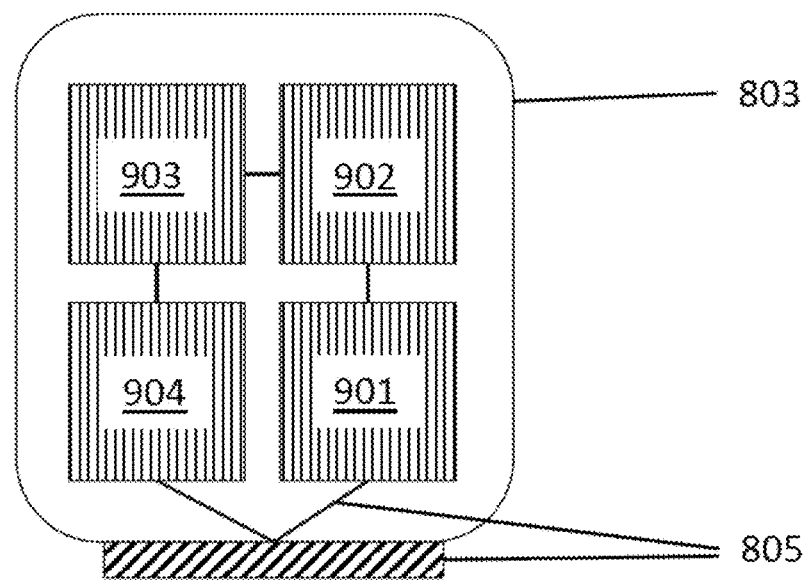
FIG. 9 shows a schematic embodiment of a modular CPU.

The system may also host a processing means 803, such as a central processing unit (CPU), for processing data. The processing means 803, may be a logic unit 803, and may be connected to the system via connection 805. As will be elaborated more below, the processing means may be dedicated for analyzing certain phenomena and may be exchangeable by the user for adjusting the system for being able to handle analysis of predetermined phenomena. An exemplary embodiment of a logic unit 803 is shown in FIG. 9. A first component may be a data processing unit 901 that processes and stores the recorded data in the memory unit 902 and attaches it to the correct time stamp and well ID. The data recorded in the memory unit 902 may comprise data recorded from each of the multiple wells in the well plate of from groups thereof. Another component is a data processing component 903, which retrieves the recorded data from a single measurement from the memory 902 and processes the data, using a predefined model, in order to determine with a certain degree of confidence which process is taking place in each of the wells measured. The data processing may be used for selecting and analyzing different phenomena, for example it may be programmed or switched for deriving information regarding toxicity of a compound for cells, an activation state of a GPC receptor, Receptor activation and inhibition such as G Protein Coupled Receptors (GPCRs), Receptor Tyrosine Kinases (RTKs), Ion Channels (ICs), Nuclear Receptors (NRs), the dissection of signal transduction cascades, microbial biofilm formation, inhibition or destruction, viral mode of entry and total viral load. A fourth part of the logic unit is the interfacing unit 904, which will output the result of this procedure to a user or additional device through an image, text data, electronic signal or alternative. Other modules, such as drivers, may be included in further embodiments of a logic unit 803.

The system more generally may be a modular system, in which different sets of well plates and logic units may be switched and interchanged, according to the necessities of each experiment. The connections between the holder and different sets of well plates may be made compatible, which presents commercial advantages.

Figure 10:
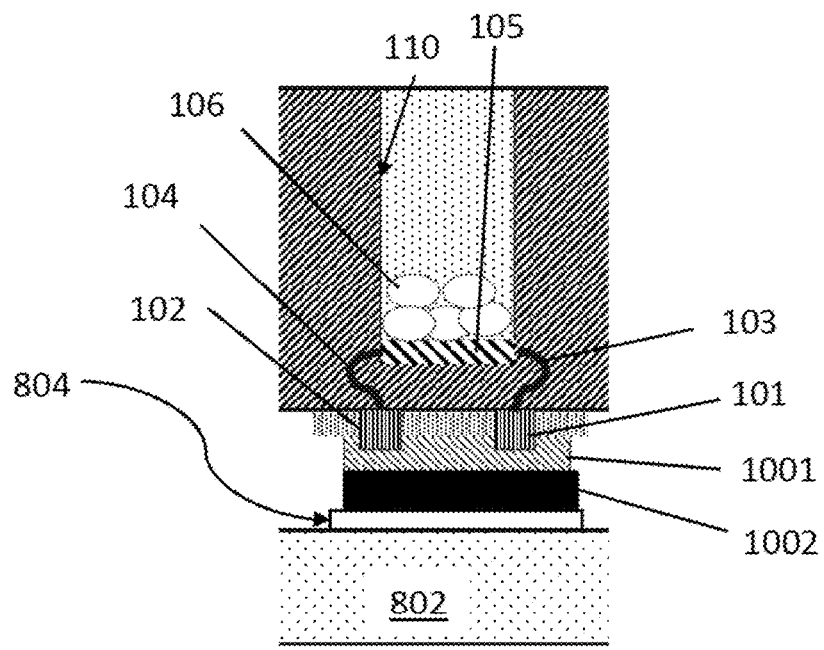
FIG. 10 shows a side view of a well according to embodiments of the present invention comprising ADC/DAC on the circuitry.

FIG. 10 further illustrates features of an embodiment of the present invention. A well plate 801 according to the present invention may comprise multiple individual wells, also referred to as contention means 110 and a connector 804 or other means to transfer electrical signals from the individual wells in the plate to the base unit 802. On the bottom of each individual well an array 105 comprising a set of 2 or more electrodes (gold, gold plated or any other suitable material) will be present. A signal (e.g. current or potential) is applied between at least 2 of the individual electrodes in the electrode arrays 105 present at the bottom of the well. This will be done using an individual DAC 1001, e.g. located underneath the well plate, although other embodiments may present a DAC distant from the well plate. This DAC will be connected using individual connection points 101, 102 as well as conducting leads 103, 104 to the electrode arrays 105 located at the bottom of the well plate. Simultaneously, the resulting current (and/or the potential signal) generated between both of the electrode arrays is recorded and digitized using an ADC 1002. This ADC can be located in the same housing as the DAC 1001, but also in a different housing. Both ADC as well as DAC can be located directly underneath each individual well, but a distant location of any or both converters is possible as well. The analog and/or digital signals can be transferred through the connector 804 to the cradle unit 802 and further on to the CPU or any other logic unit. The signal applied can be generated either in the logic unit, in the base unit 802 or in the well plate itself.

Thus, as shown in FIG. 10, driving and/or read-out circuitries can be positioned under the different wells or under the different groups of wells under the well plate when the well plate is positioned in the well plate holder. Electrical circuits can be short and substantially the same for the different wells or different groups of wells.

As indicated above, by providing individual driving and/or read-out circuitries under different wells or different groups of wells, the different wells or different groups of wells can be addressed in parallel. The latter results in a decrease of the overall measurement time. No crosstalk occurs between the different measurement wells.

These driving and/or read-out circuits may be configured for reading out different well or different groups of wells in parallel in time, i.e. simultaneously.

In preferred embodiments, measurements of the bioparticle response in the individual wells can be performed in exactly the same way by connecting each of the measuring wells in an identical way to the data acquisition device. This is done by locating the data acquisition electronics under each individual well in the plate and connecting it to the well electrodes in exactly the same way.

In another aspect, the present invention regards a substrate, such as for example a well plate or a substrate comprising a plurality of stacked wells. The substrate comprises wells, or more generally contention means, for introducing samples, such as biological samples, and for performing electrical measurements, e.g. electrochemical measurements.

According to embodiments of the present invention, for at least two individual wells or at least two groups of wells, the system comprises at least two electrodes per well for electrically characterizing an electrical parameter of bioparticles in a well, electrical leads for providing a conductive path through the substrate between the electrodes of each well and electrical connection points at a back of the substrate, and electrical connection points for connecting the at least two individual wells or at least two groups of wells separately to a driving and/or read-out circuit.

It will be understood that the specific materials used for the substrate or the specific shape or number of wells is not limiting for embodiments of the present invention.

By using connection points at the back of the substrate more homogeneous electrical connection characteristics for each of the wells can be obtained.

By way of illustration an exemplary individual well is schematically depicted in FIG. 1 showing a part of a substrate 100 comprising a well with two individual electrodes connection points 101, 102 and two conducting leads 103, 104 providing electrical contact between the connection points 101, 102 and an sensing element 105, such as an electrode array, for characterizing a parameter (in this case an electrical parameter), e.g. the value of a predetermined electrical parameter such as impedance, capacitance, inductance, resistance, etc. of bio-particles of a sample 106, for example cells, exosomes, virus, organelles, etc. According to embodiments of the present invention the electrical connection points that will be used for driving and/or reading out the measurement data are positioned at the backside of the substrate (this specific position not being shown in the schematic representation of FIG. 1 but shown in further drawings), e.g. well plate, and these are connected with the electrodes via the conducting leads which pass through the substrate. The array 105 of the particular example shown in FIG. 1 is an interdigitated array of electrodes, but any other suitable array may be used. The bioparticles 106 may be provided on the electrode array 105 for measurement, which are positioned in the well. The well typically also has upstanding walls to avoid displacement outside the array or cross-contamination.

Figure 2:
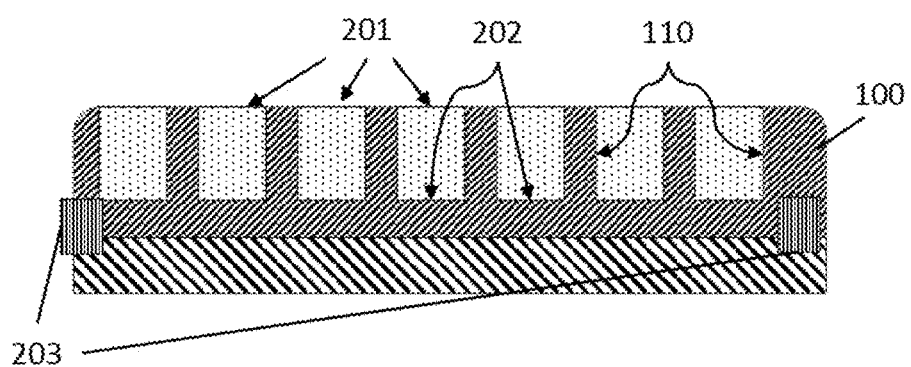
FIG. 2 shows the side view of a substrate comprising a plurality of wells.

FIG. 2 shows the section of an exemplary substrate 100 comprising a plurality of wells 201 with upstanding walls 110. The bottom 202 of each well 201 may comprise the electrode array of FIG. 1. Other embodiments may comprise a stack of connectable wells, through which conducting leads may be also provided.

In embodiments of the present invention, conducting leads 103, 104 provide a conductive path through the substrate 100 of the substrate to the back of the substrate, for allowing connection of sensing elements 105 on top of the substrate with further circuitry at the back of the substrate, such a driving circuit, read-out, analog-to-digital converters (ADCs), digital-to-analog converters (DACs), combinations thereof, etc.

Figure 3:
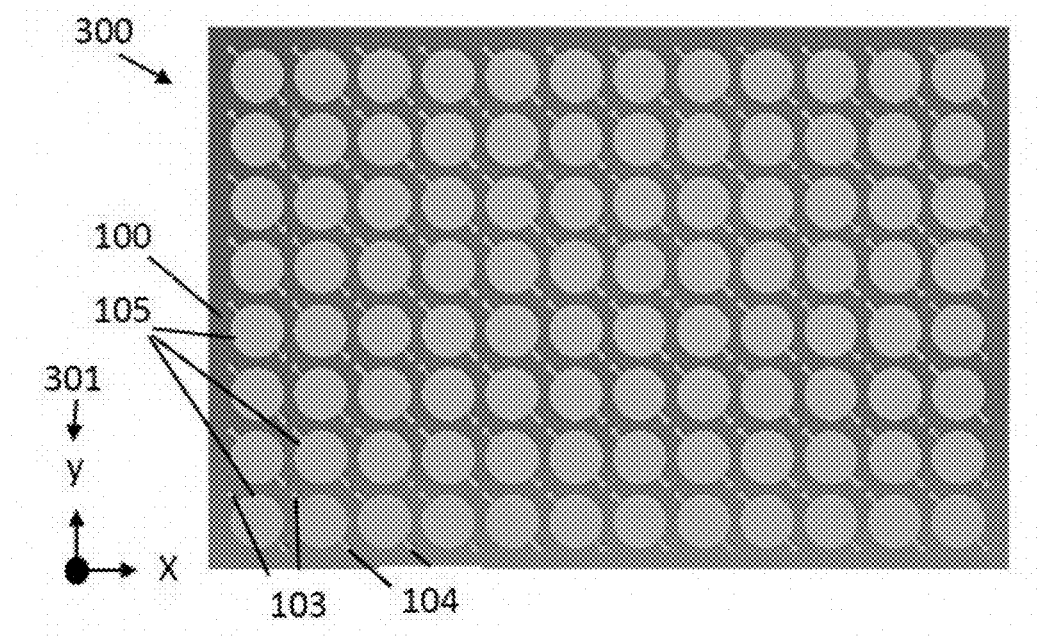
FIG. 3 shows the front side of a substrate according to embodiments of the present invention.

FIG. 3 shows a substrate 300 in top view. The surface of the plate 300 is covered with a plurality of wells comprising sensing elements 105. For example, in the present embodiment the sensing elements 105 may be a plurality of electrode arrays. The plurality of electrode arrays may be evenly distributed, for example in columns and rows, as shown in the FIG. 3, such as 12×8 columns and rows, but any other suitable distribution (e.g. hexagonal, linear, etc.) and number of wells are also allowed. Each electrode array is connected to a couple of conducting leads 103, 104 going through the substrate 100 towards the connection points 101, 102 shown in FIG. 4.

Figure 4:
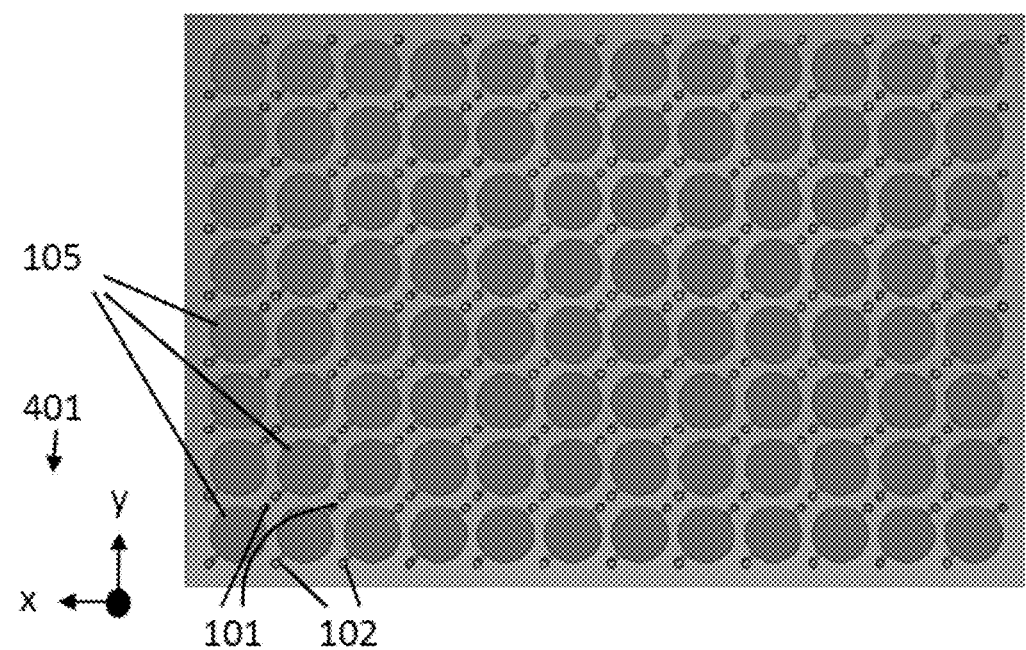
FIG. 4 shows the back side of a substrate according to embodiments of the present invention.

FIG. 4, thus, shows the back view of the well plate. The individual connection points 101, 102 are shown in the back of the plate 300. The electrode arrays 105 are placed in the opposite (top side) surface of the well plate. The conducting leads provide the electric contact between the connection points and the electrode array 105 through the substrate 100.

Figure 5:
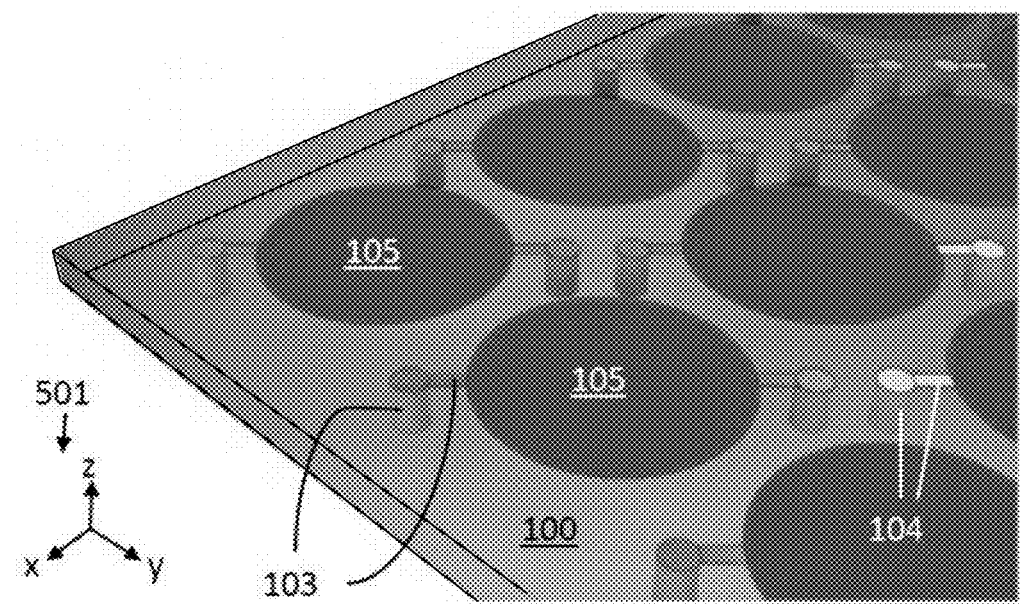
FIG. 5 shows the perspective of the front side of a substrate according to embodiments of the present invention.

This connection through the substrate is shown in FIG. 5 in a top perspective view. In this figure, a transparent view of the substrate 100 is shown. The conducting leads 103, 104 are provided on top and within the substrate, for example as a via. The plurality conducting leads may have each the same length. The use of wires of different lengths, for connecting each electrode array to further circuitry, is not necessary, which reduces space and increases density of the wells, as well as reduces differences in the signals carried by the conductors. Thus, no matter in which position of the device the electrode array is, the characteristics of the same signal through the leads will be the same for each electrode array, because no difference in the length of leads exists. Thus, any driving or measurement signal will not be influenced by different resistivities of the lead. Parallel measurements can be accurately performed, which saves time, and the need of calibration for each electrode array may be reduced or even removed.

Each of the connection points 103, 104 may be individual for each of the wells, for example for two individual wells or two groups of wells, and they may be provided substantially below the individual wells, where separate driving circuit or a read-out circuit may be provided. Thus, in some embodiments wherein connection points are provided for all individual wells, each and every well will have the same electric characteristics (same self-inductance, same losses, same resistance), which provides a very homogeneous connectivity to further circuitry, resulting in an improvement of electronic signal and data quality.

In this way, the differences in the circuits for driving and/or read-out circuitry for the different wells are reduced or even avoided, thus reducing the need for calibration. While in prior art devices, one or more wells need to be dedicated to calibration if accurate measurements are to be performed, in the present invention more or all wells may be used for actual measurements.

Figure 6:
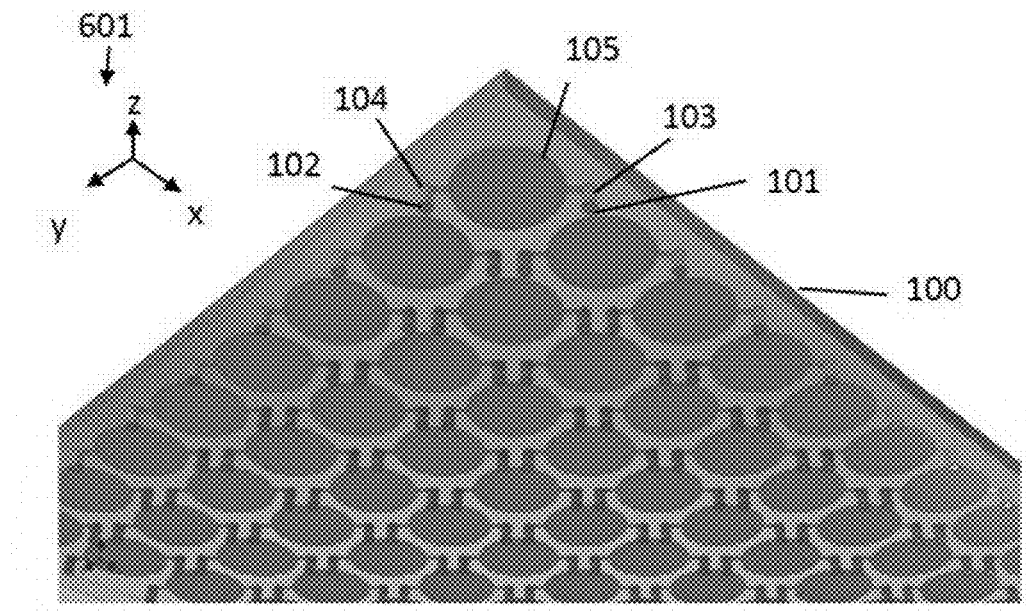
FIG. 6 shows the perspective of the back side of a substrate.

The distance between individual wells, or between the individual wells within the same group, may be homogeneous. The distance between the sensing area (e.g. the wells) and the connection to any further (driving and/or read-out) circuitry may be the same for all the wells, and may be short, for example as wide as the substrate 100 of the plate. FIG. 6 shows the transparent back perspective view of a plate, showing the connection points 101, 102 connected to the sensing elements 105 through the conducting leads, forming a via through the substrate 100.

In some embodiments (not pictured), the conducting leads may not run on top of the substrate at all. In such cases, the leads may directly connect the electrode array or sensing element through the substrate to the back side of the plate.

The plate may comprise contention zones, such as depressions, convexities, or even blind holes 201 such as those shown in FIG. 2, and the sensing element (e.g. an electrode array) may be attached, removably attached, deposited or in general placed at the bottom of these zones. The conducting leads may directly connect any sensing element at the bottom of such depressions to one or more connection points.

The plate may also be substantially flat. It may be a laminated plate. The plate material may be a polymeric, glass, composite, Teflon or semiconductor material based substrate or may be made of any other suitable material.

Figure 7:
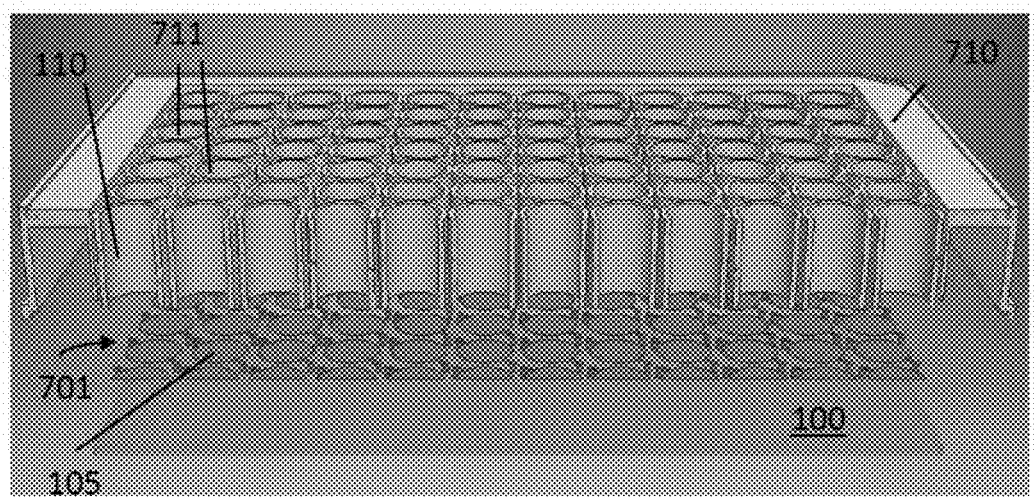
FIG. 7 shows an exploded view of a plate well according to some embodiments of the present invention.

FIG. 7 shows an exploded view of a particular embodiment of the present invention illustrating a bottom part of the well plate, the sensing layer 701 comprising sensing elements 105 such as electrode arrays and further comprising conducting leads and connection points, and illustrating the walls of the wells. A part of the substrate comprises a plurality of structures which shall serve as contention zones, for example a plurality of hollow cylinders, which may be polymeric, glass, composite, teflon, and the like. The present invention may use any other suitable shape, for example prisms for increasing density and packaging, and the distribution and forming materials may be chosen in order to increase or decrease thermal contact between each measurement zone.

According to some embodiments, the substrate also may comprise an environmental parameter sensor for measuring temperature (such as via a thermocouple, thermopile, infrared sensors, etc.), humidity, CO2 content, pH, oxygen content, nutrient concentration, salinity, illumination, etc. The additional sensor or sensors thus may directly measure the environmental parameter in the substrate. The latter may be advantageous as it allows determination of the parameter close to the position where the biological particles are evaluated.

As indicated above, it is an advantage of the present invention that all the sensors may connect to further read-out/driving circuitry using conducting leads, having all substantially the same length, through the substrate 100.

Even if the connection points for a number of wells are grouped, these are, according to embodiments of the present invention, selected such that the variability in length of the electrical paths is significantly smaller than in conventional well plates. Since the variability in the length of the electrical connections is smaller, more accurate measurements can be obtained. By providing different connection points for the different wells, parallel measurements can be performed. Furthermore, since the length of the electrical connections can be similar or the same for the different wells, there is no need for a very accurate calibration is reduced or removed.

In a third aspect, the present invention comprises a system for performing measurements for example electrochemical measurement, on samples such as biological samples, in a defined environment. The system comprises an incubator for performing electrochemical measurements in a defined environment and a substrate holder as described above. The system also comprises a plurality of driving and/or read-out circuitries for separately driving and/or reading out different wells or groups of wells through different circuitries. The system also comprises an electrical connecting means for connecting said plurality of driving and/or read-out circuitry with different electrodes of individual wells or different groups of wells of the substrate by connecting to their different electrical connection points at a backside of the substrate.

Further features and advantages of embodiments of the present invention may correspond with features and advantages of embodiments of the first aspect.

Whereas in embodiments of the first aspect, second aspect and third aspect, substrates and systems are described wherein optionally environmental parameters are sensed and taken into account, the present invention in one aspect also relates to substrates and systems wherein the electrical path lengths for the different wells or groups of wells are as known from conventional well plates, but wherein the substrate or the systems are characterized in that an environmental parameter sensor for sensing an environmental parameters. Such environmental parameters may be one or more of a temperature, a humidity, a $CO_2$ level, an $O_2$ level, a pH, a salinity, a nutrient concentration, and a degree of illumination. The system may be adapted for taking into account such a measured environmental parameter for further processing the obtained measurements. As indicated above, an environmental parameter sensor may be a temperature sensor, a gas content or composition sensor, a humidity sensor, an irradiation sensor, a pH sensor, a salinity sensor, a sensor for determining a nutrient concentration, etc. One particular example may be a thermocouple Pt100, but other sensing elements can also be used. Measurement of the conditions advantageously allows to deal with changing conditions in the incubator changing over time or with location of the substrate in the volume. The system may allow for continuous or repetitive measuring of the temperature of the cultures prior to and during the period the data is collected. Advantageously, the system is capable to record impedance data, but also of, simultaneously, measuring and storing environmental parameters using a sensor embedded in or near the well plate or in the incubator. This temperature data will then be used in the second phase for the interpretation of the recorded data. It will represent an input to the algorithm and decrease the uncertainty on the output of the device.

In still another aspect, the present invention relates to a system for measuring electrical characteristics of bioparticles, whereby the system comprises an incubator for performing electrochemical measurements in a defined environment, a substrate holder positioned in said incubator for holding a substrate comprising a plurality of wells, and wherein the system comprises a switchable or replaceable processing means adapted for receiving the electrochemical measurement data and for deriving information regarding a specific phenomenon. The system thus may be adapted so as to use a dedicated processing means wherein the dedicated processing means is adapted for deriving information regarding a specific phenomenon. In this way, the system can be easily tuned, by switching the dedicated processing means, to detection of a specific phenomenon. Examples of different phenomena for which a dedicated processor may be provided are toxicity of a compound for cells, receptor activation and inhibition, dissection of signal transduction cascades, microbial biofilm formation/inhibition/destruction, and viral mode of entry and/or total viral load. It is an advantage of embodiments of the present invention that, by using dedicated processing means, the accuracy and reliability of the generated data and analysis can be high. Furthermore, according to some embodiments additional robustness can be obtained by the device no longer providing time graphs containing time series of impedance-related values, but directly a decision on the phenomenon taking place and the significance of this decision. This is achieved by including the interpretation of the EIS signals obtained in the equipment.

It thereby is an advantage that the substrate holder used for locating, fixing and contacting the well plate can be used for all types of investigations. To this substrate holder however a specific CPU unit needs to be connected that is specific for the type of phenomenon that is to be investigated. So in order to switch the phenomenon to be analyzed, simply another processing means can be connected to the substrate holder. This gives a research lab the flexibility to evolve over time, but also allows cost reduction by reducing the amount of skilled staff required in e.g. drug development process.

According to some embodiments of the present invention, analysis of the data, e.g. time series of data, can be performed in an automated way. This is possible by a new approach where the impedance-measuring device is no longer usable for various, broad-scale investigations, but rather focuses on identifying a specific processes. The system, in some embodiments, therefore does not longer provide time graphs containing time series of impedance-related values, but merely a decision on what the nature is of the phenomenon taking place and the significance of this decision. This is achieved in some embodiments by including the interpretation of the (evolution of the) EIS signals obtained in the equipment. To avoid this interpretation being obscured by external influences the interpretation algorithm may take into account the environmental parameters. As such, according to some embodiments, the system will collect impedance data simultaneously with other data such as environmental parameters and the data feed of both sources in interpretation algorithms in order to produce trustworthy decisions.

In yet another aspect, the present invention also relates to a computer program product for deriving information on a phenomenon. According to embodiments of the present invention, the computer program product is adapted for receiving information on a measurement of electrical characteristics of bioparticles and information on at least one of the following: an environmental parameter measured at the substrate, or a determined moment when the active compound was added to the bioparticles. The computer program product furthermore being adapted for processing said received information for deriving information regarding said phenomenon. By taking into account environmental parameters that were present during the electrical characteristics measurements and/or a moment of addition of the active compound, more accurate information regarding the phenomenon under study.

By way of example, embodiments of the present invention not being limited thereto, the phenomenon under study may be one or more of toxicity of a compound for cells, receptor activation and inhibition, dissection of signal transduction cascades, microbial biofilm formation/inhibition/destruction, and viral mode of entry and/or total viral load. Receptor activation and inhibition may include activation and inhibition of G Protein Coupled Receptors (GPCRs), of Receptor Tyrosine Kinases (RTKs), of Ion Channels (ICs) or of Nuclear Receptors (NR).

The computer program product may be stored on a processor. One configuration of such a processor may for example include at least one programmable computing component coupled to a memory subsystem that includes at least one form of memory, e.g., RAM, ROM, and so forth. It is to be noted that the computing component or computing components may be a general purpose, or a special purpose computing component, and may be for inclusion in a device, e.g., a chip that has other components that perform other functions. Thus, one or more aspects of the present invention can be implemented in digital electronic circuitry, or in computer hardware, firmware, software, or in combinations of them. For example, each of the functions of the devices or systems as described above may be a computer implemented step. Thus, while a processor as such is prior art, a system that includes the instructions to implement aspects of the functions of the devices or systems as described above is not prior art. The present invention thus also includes a computer program product which provides the functionality of any of the devices or systems according to the present invention when executed on a computing device.

In another aspect, the present invention relates to a data carrier for carrying a computer program product for performing electrical measurements of bioparticles, e.g. using a system or device as described above. Such a data carrier may comprise a computer program product tangibly embodied thereon and may carry machine-readable code for execution by a programmable processor. The present invention thus relates to a carrier medium carrying a computer program product that, when executed on computing means, provides instructions for executing any of the functions as described for the devices and systems as described above. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fiber optics, including the wires that comprise a bus within a computer.

In another aspect, the present invention also relates to a method for measuring electrical characteristics of bioparticles. The method comprises continuously or regularly measuring electrochemical data on the bioparticles in a defined environment, comparing the continuously or regularly measured electrochemical data with reference data, determining a moment for adding an active compound based on said comparison, and adding the active compound on the determined moment.

In still another aspect, the present invention relates to a computer program product for performing a method for measuring electrical characteristics of bioparticles as described above.

By way of illustration, embodiments of the present invention not being limited thereto, exemplary results are shown illustrating the possibility of characterization of cells in suspension.

It was surprisingly found that by using of broad spectrum electrochemical impedance spectroscopy, monitoring of the growth of cells in suspension can be performed, in the present example being suspended mammalian cells. Whereas it is known to monitor growth of cells using electrochemical impedance spectroscopy for adherent cell cultures, this is not the case for suspended cell structures. Good characterization can according to embodiments of the present invention be performed by using appropriate frequencies, which can be determined if a broadband spectrum is recorded and by using not only the magnitude of the impedance (|Z|) but also taking into account the phase angle of the impedance ($\Theta$). These values are defined by the equation below, while disregarding the phase angle.

$$Z=|Z|e^{i\Theta}$$

Figure 11:
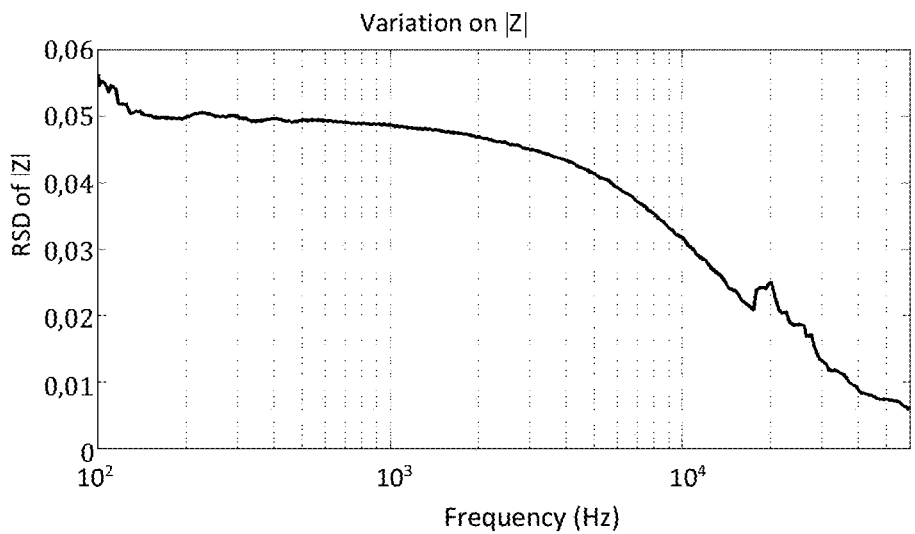
FIG. 11 shows the relative standard deviation of |Z| between 100 Hz and 60 kHz obtained by recording the impedance spectrum every 30 minutes of a Jurkat cell culture, of 20000 initial cells, that is left to grow for 24 hours, illustrating characteristics of embodiments of the present invention.
Figure 12:
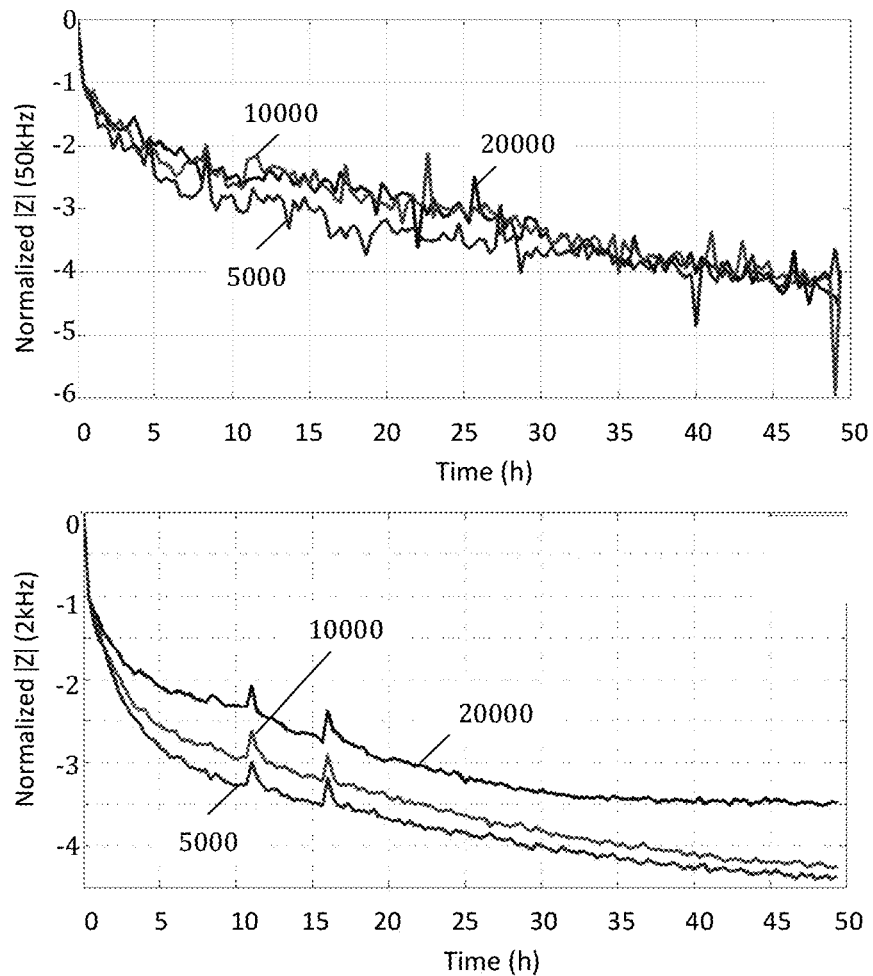
FIG. 12 shows the evolution of |Z| during cell growth of Jurkat cell cultures with initial populations of 20000, 10000 and 5000 cells, wherein (a) depicts the evolution at 50 kHz and (b) at 2 kHz, illustrating characteristics of embodiments of the present invention.

Generally monitoring the growth of adherent cells using EIS is done using |Z| at frequencies between 10 and 50 kHz. However, this does not give satisfactory results when using suspended cell cultures. The reason for this can be found by looking at the variation of |Z| during growth over a broader impedance spectrum than 10 to 50 kHz, as shown in FIG. 11. FIG. 11 shows the relative standard deviation of |Z| between 100 Hz and 60 kHz obtained by recording the impedance spectrum every 30 minutes of a Jurkat cell culture, of 20000 initial cells, that is left to grow for 24 hours. From this graph it becomes evident that the maximum effect of the cell growth on |Z| is situated at frequencies below 2 kHz and not between 10 and 50 kHz. As a result, measuring systems that use the traditional frequency band have a signal strength that it up to 5 times weaker that that obtained using the optimal frequency range. The resulting difference in sensitivity is illustrated in FIG. 12. Here it can be clearly seen that monitoring |Z| at 50 kHz does not deliver sufficient resolution to distinguish between the different cell populations. At 2 kHz this distinction is clearly visible. Although monitoring |Z| at the appropriate frequency does deliver the possibility to distinguish between different cell populations, the behavior of |Z| is declining in nature and thus not intuitively relatable to the increasing cell population.

Figure 13:
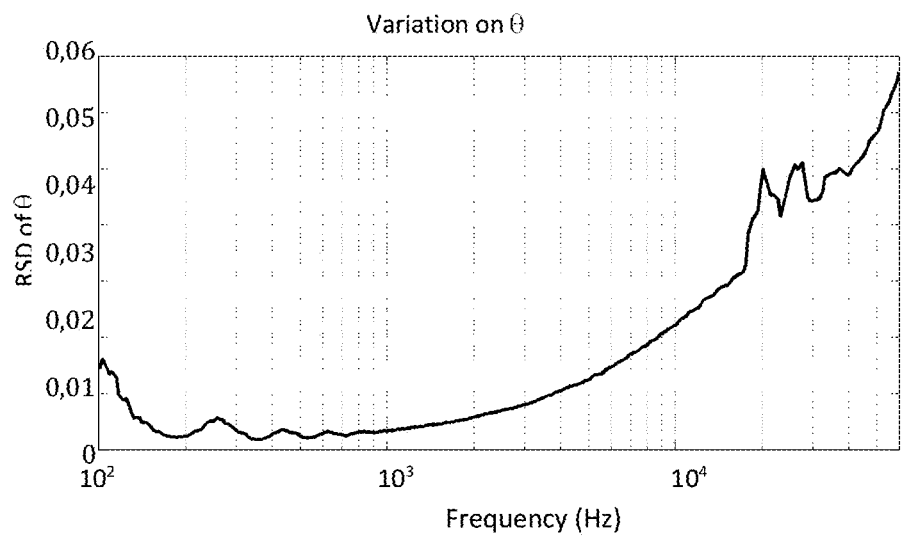
FIG. 13 illustrates the relative standard deviation of Θ between 100 Hz and 60 kHz obtained by recording the impedance spectrum every 30 minutes of a Jurkat cell culture, of 20000 initial cells, that is left to grow for 24 hours, illustrating characteristics of embodiments of the present invention.
Figure 14:
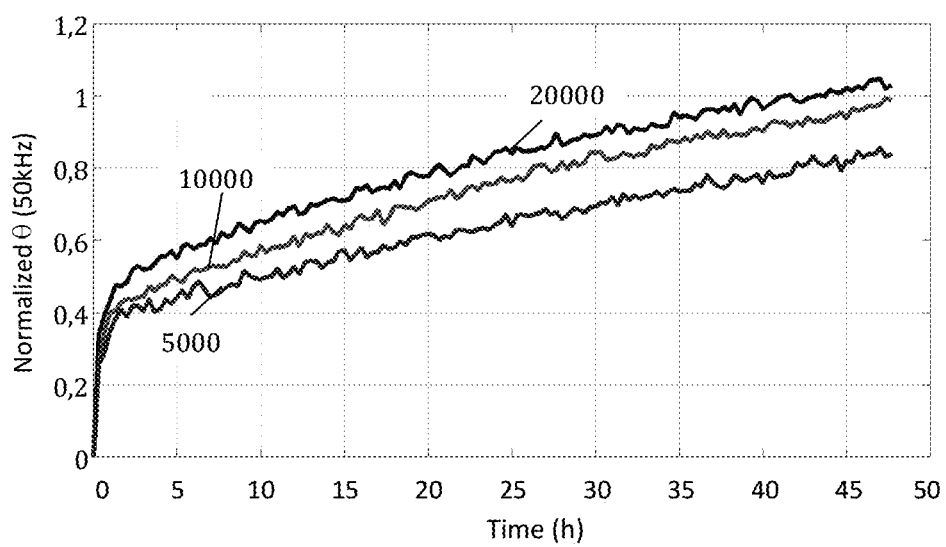
FIG. 14 illustrates the evolution of Θ during cell growth of Jurkat cell cultures with initial populations of 20000, 10000 and 5000 cells at 50 kHz, illustrating characteristics of embodiments of the present invention.
Figure 15:
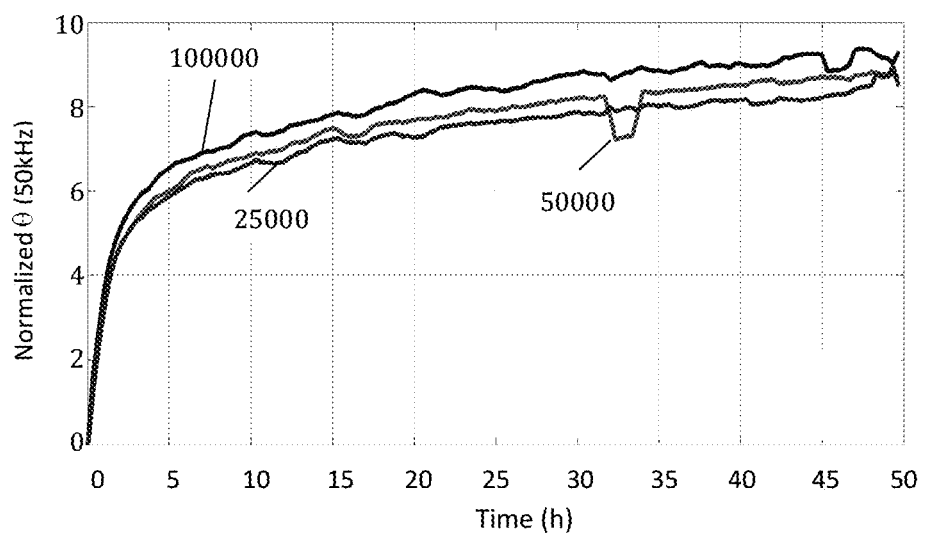
FIG. 15 shows the evolution of Θ during cell growth of PBMC cultures with initial populations of 100000, 50000 and 25000 cells at 50 kHz, illustrating characteristics of embodiments of the present invention. The drawings are only schematic and are non-limiting. In the drawings, the size of some of the elements may be exaggerated and not drawn on scale for illustrative purposes.

This can be resolved by using the $\Theta$ component of the complete impedance Z. The variation of $\Theta$ during growth over the impedance spectrum is presented in FIG. 13. FIG. 13 illustrates the relative standard deviation of $\Theta$ between 100 Hz and 60 kHz obtained by recording the impedance spectrum every 30 minutes of a Jurkat cell culture, of 20000 initial cells, that is left to grow for 24 hours. In the case of $\Theta$, frequencies above 50 kHz can be identified as those most susceptible to cell growth. This results in an evolution of $\Theta$ over time as depicted in FIG. 14. FIG. 14 illustrates the evolution of $\Theta$ during cell growth of Jurkat cell cultures with initial populations of 20000, 10000 and 5000 cells at 50 kHz. This does not only provide a clear distinction between different cell populations, but also maintains an intuitive relationship between the growing cell population and the monitored parameter. Similar results have been obtained using Toledo, Z138, BV173, MV-4-11, KG1a, Ramos and Molm13 cell lines as well as peripheral blood mononuclear cells (PBMC's). As an example of this the evolution of $\Theta$ for different cell populations of PBMC's is shown in FIG. 15. FIG. 15 shows the evolution of $\Theta$ during cell growth of PBMC cultures with initial populations of 100000, 50000 and 25000 cells at 50 kHz.

The invention claimed is:

1. A system for measuring electrical characteristics of bioparticles, the system comprising:
    an incubator configured for performing electrochemical measurements in a defined environment,
    a substrate holder positioned in said incubator and configured for holding a substrate comprising a plurality of wells,
    wherein the system is configured for continuously or regularly measuring electrochemical data,
    the system comprising a processor programmed for comparing the continuously or regularly measured electrochemical data with reference data and for determining a moment for adding an active compound based on said comparison;
    wherein the bioparticles are cells, organelles, exosomes or viruses, and
    wherein the processor is configured to determine the moment for adding the active compound based on a parameter value derived from a broad-spectrum impedance measurement conducted on bioparticles in the well, the broad-spectrum impedance measurement spanning at least a frequency range of 100 Hz to 50 kHz.

2. A system according to claim 1, wherein the system furthermore comprises a delivery input configured for automatically delivering an active compound in the well at the determined addition moment.

3. A system according to claim 1, wherein the system is adapted for measuring impedance data over a frequency span of at least two decades, at least 2 measurement points per decade being recorded.

4. A system according to claim 1 wherein the system is adapted for measuring impedance data comprising both a magnitude as well as a phase of the impedance and/or wherein the system is adapted for measuring electrochemical data on bioparticles in solution.

5. A system according to claim 1, wherein the processor is programmed for deriving information regarding a specific phenomenon or wherein the processor is programmed for determining information regarding a specific phenomenon, taking into account a determined addition moment for delivering the active compound in the well.

6. A system according to claim 5, wherein the processor is a switchable module programmed for deriving information regarding one of the following phenomena:
    toxicity of a compound for cells,
    Receptor activation and inhibition such as G Protein Coupled Receptors (GPCRs),
    Receptor Tyrosine Kinases (RTKs), Ion Channels (ICs), Nuclear Receptors (NRs),
    the dissection of signal transduction cascades, microbial biofilm formation/inhibition/destruction or viral mode of entry and total viral load.

7. A system according to claim 1, wherein said system furthermore comprises an environmental parameter sensor for sensing an environmental parameter in the incubator, the environmental parameter being one or more of a temperature, a humidity, a $CO_2$ level, an $O_2$ level, a pH, a salinity, a nutrient concentration, and a degree of illumination.

8. A system according to claim 7, wherein the processor is programmed for determining said information regarding said phenomenon, taking into account said environmental parameter.

9. A system according to claim 1, the system furthermore comprising:
a plurality of driving and/or read-out circuitries for separately driving and/or reading out different wells or groups of wells through different circuitries,
an electrical connector for connecting said plurality of driving and/or read-out circuitry with different electrodes of individual wells or different groups of wells of the substrate by connecting to the electrodes' different electrical connection points at a backside of the substrate.

10. A system according to claim 9, wherein the driving and/or read-out circuitries are positioned substantially under the different wells or under the different groups of wells under the substrate, when the substrate is positioned in the substrate holder, such that the electrical circuits can be short and substantially the same for the different wells or different groups of wells and/or
wherein the driving and/or read-out circuits are configured for reading out different well or different groups of wells in parallel in time, i.e. simultaneously and/or
wherein each driving and/or read-out circuit comprise an analog to digital converter and a data acquisition component and/or
wherein each driving and/or read-out circuit comprises an analog to digital converter and a data acquisition component whereby the system is adapted for acquiring electrochemical measurement data of a well and for processing the data not taking into account calibration data of another well in the substrate.

11. A method for measuring electrical characteristics of bioparticles, the method comprising:
continuously or regularly measuring electrochemical data on the bioparticles in a defined environment,
comparing the continuously or regularly measured electrochemical data with reference data,
determining a moment for adding an active compound based on said comparing the continuously or regularly measured electrochemical data with reference data, and adding the active compound on the determined moment,
wherein the bioparticles are cells, organelles, exosomes or viruses, and
wherein said determining the moment for adding the active compound is based on a parameter value derived from a broad-spectrum impedance measurement conducted on bioparticles, the broad-spectrum impedance measurement spanning at least a frequency range of 100 Hz to 50 kHz.

12. A method according to claim 11, wherein continuously or regularly measuring electrochemical data comprises measuring impedance data over a frequency span of at least two decades, at least 2 measurement points per decade being recorded.

13. A method according to claim 11, wherein measuring electrochemical data comprises measuring impedance data comprising both a magnitude as well as a phase of the impedance and/or
wherein the method comprises deriving information regarding a specific phenomenon and/or
wherein the method comprises deriving information regarding one of the following phenomena: toxicity of a compound for cells, Receptor activation and inhibition such as G Protein Coupled Receptors, Receptor Tyrosine Kinases, Ion Channels, Nuclear Receptors, the dissection of signal transduction cascades, microbial biofilm formation/inhibition/destruction or viral mode of entry and total viral load and/or wherein the method comprises determining information regarding a phenomenon taking into account the determined addition moment for delivering the active compound in the well.

14. A method according to claim 11, the method comprising sensing an environmental parameter in the incubator, the environmental parameter being one or more of a temperature, a humidity, a $CO_2$ level, an $O_2$ level, a pH, a salinity, a nutrient concentration, and a degree of illumination and/or
the method comprising sensing an environmental parameter in the incubator, the environmental parameter being one or more of a temperature, a humidity, a $CO_2$ level, an $O_2$ level, a pH, a salinity, a nutrient concentration, and a degree of illumination and determining information regarding a phenomenonphenomen, taking into account the environmental parameter.

15. A method according to claim 11, the method comprising reading out different well or different groups of wells in parallel in time, i.e. simultaneously and/or the method being configured for acquiring electrochemical measurement data of a well and for processing the data not taking into account calibration data of another well in the substrate.

16. A method according to claim 11, the method being adapted for monitoring growth of adherent cell cultures and/or the method being adapted for monitoring growth of suspended cell cultures.

17. A computer program product for measuring electrical characteristics of bioparticles, the computer program product being adapted for, when run on a computer, performing a method according to claim 11.

* * * * *